United States Patent
Foerster et al.

(10) Patent No.: US 8,668,696 B2
(45) Date of Patent: Mar. 11, 2014

(54) LOW FRICTION BUCKLE TIGHTENING SYSTEMS AND METHODS

(75) Inventors: Seth Arnold Foerster, San Clemente, CA (US); David Trottingwolf Aldridge, Laguna Hills, CA (US)

(73) Assignee: Dallen Medical, Inc., San Clemente, CA (US)

( * ) Notice: Subject to any disclaimer, the term of this patent is extended or adjusted under 35 U.S.C. 154(b) by 434 days.

(21) Appl. No.: 12/858,332

(22) Filed: Aug. 17, 2010

(65) Prior Publication Data

US 2014/0018807 A1 Jan. 16, 2014

Related U.S. Application Data

(60) Provisional application No. 61/235,429, filed on Aug. 20, 2009.

(51) Int. Cl.
*A61B 17/82* (2006.01)
*A44B 11/10* (2006.01)

(52) U.S. Cl.
USPC .............................................. 606/74; 24/171

(58) Field of Classification Search
USPC ........... 606/74, 103, 105, 203, 232, 324, 905; 24/171, 194, 196, 163 R; 602/19; 242/388, 388.1, 388.2
See application file for complete search history.

(56) References Cited

U.S. PATENT DOCUMENTS

| | | | |
|---|---|---|---|
| 1,234,818 A * | 7/1917 | Sturrock | 24/196 |
| 1,374,691 A * | 4/1921 | Troop | 24/196 |
| 1,914,299 A * | 6/1933 | Sauerwald | 24/194 |
| 2,743,497 A * | 5/1956 | Davis | 24/196 |
| 3,822,445 A | 7/1974 | Feng | |
| 3,965,539 A * | 6/1976 | Golden | 242/388 |
| 4,208,770 A * | 6/1980 | Takada | 24/136 K |
| 4,279,248 A | 7/1981 | Gabbay | |
| 4,444,181 A | 4/1984 | Wevers et al. | |
| 303,360 A | 8/1984 | Brunner | |
| 4,535,772 A | 8/1985 | Sheehan | |
| 4,667,675 A | 5/1987 | Davis | |
| 4,677,711 A * | 7/1987 | Anscher | 24/200 |
| 4,730,615 A | 3/1988 | Sutherland et al. | |
| 4,813,416 A | 3/1989 | Pollak et al. | |

(Continued)

*Primary Examiner* — Todd Manahan
*Assistant Examiner* — Eric S Gibson
(74) *Attorney, Agent, or Firm* — Stout, Uxa, Buyan & Mullins, LLP; Donald E. Stout (57) ABSTRACT

A tensioning device comprises an elongate member, preferably a band, and a frame having first and second sides. The band has a first end that is attachable to the first side of the frame and a second end that is releasably securable to the second side of the frame. A movable clamping member on the frame secures the second end of the band to the second side of the frame by cinching the second end of the band between an engagement surface on the band and a mating engagement surface on the second side of the frame. A restraining member is provided for restraining the clamping member to a first position spaced from the mating locking surface on the second side of the frame, when the restraining member is in a restraining orientation. The restraining member is movable out of the restraining orientation after the band is tensioned to a predetermined level using the second end. The band is tensioned to the aforementioned predetermined level and is secured to the second side of the frame, so that the band establishes a path of tension along its length that extends linearly between the two ends of the band.

12 Claims, 7 Drawing Sheets

(56) References Cited

U.S. PATENT DOCUMENTS

| | | | |
|---|---|---|---|
| 4,901,721 A | 2/1990 | Hakki | |
| 4,903,378 A * | 2/1990 | Kasai | 24/196 |
| 4,938,760 A | 7/1990 | Burton et al. | |
| 4,959,064 A | 9/1990 | Engelhardt | |
| 4,969,892 A | 11/1990 | Burton et al. | |
| 5,330,489 A | 7/1994 | Green et al. | |
| 5,339,870 A * | 8/1994 | Green et al. | 140/123.5 |
| 5,366,461 A | 11/1994 | Blasnik | |
| 5,571,105 A | 11/1996 | Gundolf | |
| 5,722,976 A | 3/1998 | Brown | |
| 5,797,915 A | 8/1998 | Pierson, III et al. | |
| 5,807,214 A | 9/1998 | Riazi | |
| 5,810,854 A | 9/1998 | Beach | |
| 5,849,012 A | 12/1998 | Abboudi | |
| 5,972,006 A | 10/1999 | Sciaino, Jr. | |
| 6,051,007 A | 4/2000 | Hogendijk et al. | |
| 6,066,160 A | 5/2000 | Colvin et al. | |
| 6,068,646 A * | 5/2000 | Lam | 606/203 |
| 6,070,823 A * | 6/2000 | Clary | 242/388.1 |
| 6,080,185 A | 6/2000 | Johnson et al. | |
| 6,471,715 B1 | 10/2002 | Weiss | |
| 6,540,769 B1 | 4/2003 | Miller, III | |
| 6,547,725 B1 | 4/2003 | Paolitto et al. | |
| 6,589,246 B1 | 7/2003 | Hack et al. | |
| 6,648,903 B1 | 11/2003 | Pierson, III | |
| 6,833,001 B1 * | 12/2004 | Chao | 606/203 |
| 6,969,398 B2 | 11/2005 | Stevens et al. | |
| 6,997,189 B2 | 2/2006 | Biggs et al. | |
| 7,108,710 B2 | 9/2006 | Anderson | |
| 7,163,540 B2 * | 1/2007 | Martello | 606/319 |
| 7,341,558 B2 | 3/2008 | de la Torre et al. | |
| 7,416,556 B2 | 8/2008 | Jackson | |
| 7,722,632 B2 | 5/2010 | Rothstein et al. | |
| 7,867,251 B2 | 1/2011 | Colleran et al. | |
| 7,867,253 B2 | 1/2011 | McMichael et al. | |
| 2002/0147449 A1 | 10/2002 | Yun | |
| 2003/0093117 A1 | 5/2003 | Saadat | |
| 2005/0075653 A1 | 4/2005 | Saadat et al. | |
| 2005/0090827 A1 * | 4/2005 | Gedebou | 606/72 |
| 2005/0149121 A1 | 7/2005 | Crombie et al. | |
| 2005/0240203 A1 | 10/2005 | Fuseri et al. | |
| 2005/0251209 A1 | 11/2005 | Saadat et al. | |
| 2007/0073289 A1 | 3/2007 | Kwak et al. | |
| 2007/0112385 A1 | 5/2007 | Conlon | |
| 2007/0213725 A1 | 9/2007 | Hack | |
| 2007/0276437 A1 | 11/2007 | Call et al. | |
| 2007/0293863 A1 | 12/2007 | Reimels et al. | |
| 2007/0293864 A1 | 12/2007 | Reimels et al. | |
| 2008/0004624 A1 | 1/2008 | Olroyd | |
| 2008/0015589 A1 | 1/2008 | Hack | |
| 2009/0062853 A1 | 3/2009 | McMichael et al. | |
| 2011/0313435 A1 * | 12/2011 | Aldridge et al. | 606/151 |
| 2012/0101526 A1 * | 4/2012 | Bennett | 606/232 |

* cited by examiner

LOW FRICTION BUCKLE TIGHTENING SYSTEMS AND METHODS

This application claims the benefit under 35 U.S.C. 119(e) of the filing date of Provisional U.S. Application Ser. No. 61/235,429, entitled Low Friction Buckle Tightening System, filed on Aug. 20, 2009. This application is also related to co-pending and commonly assigned U.S. patent application Ser. No. 12/347,821, entitled Dynamic Suture Tensioning Device, filed on Dec. 31, 2008, Ser. No. 12/406,902, entitled Knotless Dynamic Suture Tensioning Device and Methods, filed on Mar. 18, 2009, Ser. No. 12/406,904, entitled Load Shaping for Dynamic Tensioning Mechanisms and Methods, filed on Mar. 18, 2009, Ser. No. 12/406,909, entitled Dynamic Tissue Holding Device with Low Profile Spring, filed on Mar. 18, 2009, Ser. No. 12/815,989, entitled Suture Band Buckle and Methods, filed on Jun. 15, 2010, and Ser. No. 12/836,000, entitled Flat Suture Banding System and Methods, filed on Jul. 14, 2010. All of the foregoing applications are expressly incorporated herein by reference, in their entirety.

BACKGROUND OF THE INVENTION

The present invention is related to the general surgical repair of separated body tissues, and more particularly to internally fixating and stabilizing such body tissues, specifically bones.

In the present state of the art, there are a number of systems available to repair biological tissues separated in surgery or by injury. These products serve to approximate and stabilize the tissues so that healing may commence and provide compression in the interface to promote healing. Compression and stability are critical for proper anatomical healing of tissue. With the correct amount of compression applied to the interface of the tissue portions to be joined, signals are sent to the tissue, thus allowing the tissue to remodel in proper anatomical position. The amount of compression applied to the tissue interface needs to be appropriate to the type of tissue that is being healed.

Twisted wires are also typically used to keep bone fragments together so they may heal. Twisted wires only hold tension as long as the twisted wire pair remains stable. Often the wires untwist too soon failing to keep the bone fragments together so that they may heal. Wires can also cut into the bone fragments allowing them to separate so that healing is difficult.

When it is necessary to access the thoracic cavity for a medical procedure, for example, it is required to cut the sternum into two pieces using a sternal saw. Once the procedure is completed within the thoracic cavity, the sternum must be repaired. For such repairs, it is known to use a dynamic compression device. Some of the drawbacks of this typical device, and others which are used include:

1. Bulky spring materials, while occupying substantial space, often do not store much energy. Some use polymer elastic bands, while other use coiled springs;

2. Wires are sometimes used to wrap the bones into position in compression with one another. However, wires can have sharp ends that can damage adjunctive tissues. Knot stacks in suture can interfere with the natural movement of surrounding tissues; and 3. Current banding systems that incorporate a biasing mechanism to achieve dynamic compression put the biasing mechanism in line with the band or suture. This practice competes with precious space at the healing site. Suture or bands are used to approximate tissues so that they may heal. It is desirable to obtain the best purchase possible on the tissue, so that the binding mechanics offered by the suture may be utilized. The best purchase is optimized by ensuring that the suture has the greatest contact area with the tissue. If a biasing mechanism is interfering with this concept, the biasing mechanism may diminish the suture's ability to hold the tissues together.

In addition, the current banding systems have stiff bands that are not compliant with bony undulations. Flat sutures are used, but are tedious to tie and do not hold reliably.

Bands address the issues wires have in the following discussion. A band, by definition, is wide. In being wide, a band distributes its forces over a wider surface area. This inhibits the band from digging into the bone. In being wide, a band affords a larger cross-sectional area whereby more material may be realized thus presenting the opportunity to offer as much strength in the construct as is necessary to hold the bone fragments together. As such, bands address wire's two main weaknesses, namely, digging into the bone fragments being held together and, not having sufficient cross sectional area.

Bands bring in other attributes other than strength and reduced pressure on the bone. Some of these attributes are difficult to manage. With strength comes stiffness, as mentioned elsewhere herein. The larger cross-section of the band significantly increases the stiffness of the band. While stiffness and rigidity are good attributes in that they can stabilize the bone union, these attributes can also prevent the band from following the contours of the bone when inserted. This can lead to capturing tissues underneath the band that ultimately destabilize the union as the tissues continue to compress and disappear over time.

Binding the band ends together can also impose some problems. Generally this involves a mechanism on one band end that interfaces with holes or slots or contours on the other band end. This creates a tensioning system that is incremental in nature. As in the twisted wire system, this mechanical interface of the two ends is the weakest link in the system. This mechanical interface becomes stronger as the incremental steps become larger. But larger incremental steps aren't conducive to fine tuning the tension, so this is problematic. Flat sutures have been used to tie tissues together but the residual tension supplied in such a knotted structure is insufficient for optimum healing. There is a lot of fuss/time associated with trying to keep and hold a desirable tension with these flat sutures. What is needed is an attachment means that provides variable tensioning.

Buckles are commonly used to adjust the effective length of a strap or band. Such strap/buckle combinations are commonly used on seatbelts, helmet chin retainers, and shoulder straps. The adjustability of the buckle makes the strap much more functional in these applications. Seatbelts can be adjusted to fit different sized people, helmets can be cinched on tightly and then taken off, and backpacks can be worn by different sized people because the shoulder straps adjust.

There are applications where a buckle may be used in combination with a strap when re-adjustment is not as critical as the first adjustment. This would be an application where the first length adjustment of the strap is critical and closely tied to a specific tension in the strap. Such a feature could add cost and complexity to the buckle. But given the application, the added cost and complexity would be worth its added benefits.

There are many fastener inventions that trade off reversibility of the fastener for functionality. Screws, for example, can attach objects to gypsum board and come out easily if needed. Unfortunately, screws don't hold very well in gypsum board. Toggle bolts don't come out easily, but hold objects rather well to gypsum board. So toggle bolts overcome a screw's lack of holding power in gypsum board at the expense of reversibility.

In the realm of fasteners, screws have insufficient surface area to work well in gypsum board. This deficiency enables the invention of the toggle bolt. This is analogous to the present invention. The common buckle has too much friction in it to be affective in certain applications. A modified version of the same buckle that adds some user complexity and sacrifices the easy re-use of the buckle is preferable in these certain applications.

Consider tying down a cargo load. A strap with a buckle is considered in many cases to not be able to apply sufficient tension to the strap to make the load stable. Many users resort to a complicated ratcheting system that can easily over-tension the load and damage it. Most light cargo loads would benefit from a buckle system that has double the tensioning abilities of the common buckle. This would add some user complexity, but not the user complexity, or cost, realized in a strap ratcheting system.

A low friction buckling system for tying down cargo loads is a re-usable use of this fastener invention. There are, however, single use applications for the invention. Consider straps used for approximating tissues after they have been separated during surgery. A common buckle hardly has the ability to pull the tissue parts together without an external tensioning device. The present modified, low friction buckle invention makes it possible to not only approximate the tissues easier, but to significantly realize more tension in the suture with an external tensioning device.

The low friction buckle systems of the present invention are therefore attractive for use in sternal closure because they offer some distinct advantages over the twisted wires and ordinary buckle systems most commonly used in the procedure.

The present invention thus addresses one or more of the issues discussed above.

SUMMARY OF THE INVENTION

The present invention pertains to a tensioning device for holding separated tissues in contact with one another, with a means to increase tensioning by reducing friction. The invention is applicable to other non-surgical environments as well, basically applying to any setting wherein it is desired to clamp two separated members together using a buckle arrangement.

The present devices comprise a frame or a buckle frame. The frame may be rigid and has two opposing first and second sides and a lower surface and/or lower side and an upper surface and/or upper side. The lower surface and/or lower side of the frame is the surface and/or side that is in contact with the tissue(s) being held together. In one embodiment, the two opposing first sides of the frame may be parallel to one another. The device further comprises an elongate member or suture or band for extending through and/or around the separated tissues to be held together in conjunction with said frame. The elongate member or suture or band has a first end, that is secured to the first side of the frame and a second end that is releasably securable to the second side of the frame. The device also comprises a floating/moveable clamping member on the frame which is adapted to secure the second end of the elongate member to the second side of said frame by cinching the second end of the elongate member between its surface proximal to the second side of the frame and a mating locking surface on the second side of the frame. The device further comprises a means to contain movement of the floating/movable clamping member towards the mating locking surface on the second side of the frame, the means being adapted to be removable after the elongate member is first tensioned using the second end. In this device, after the elongate member is tensioned in a first tensioning step and is secured to the second side of said frame, said elongate member establishes a path of increased tension along its length that extends linearly between the two ends of the elongate member relative to the tension when such means to contain movement of said floating/movable clamping member towards a mating locking surface on said second side of the frame is not present in the device.

In one embodiment, the elongate member is a band or suture and is sufficiently flexible to provide tension along its length. In yet another embodiment, the elongate member, band or suture is substantially flat. Also, independently, in one embodiment, a needle may be secured to either the first or second end of the band or suture of the device. Preferably, the frame or buckle has an opening that is sized appropriately to allow the passage of a needle that is secured to an end of the band or suture. In addition, the surfaces of the frame, for example, the surfaces of the interior of the frame, are adapted to guide the band so that the band can be easily threaded into the frame or buckle. As discussed below, the surface of the clamping member and the corresponding mating locking surface on the frame may be textured or roughened for holding the band more securely once tensioned.

The inventive device may have a floating/movable clamping member with a circular cross section. In this instance, the device may further comprise a means to prevent the floating/movable clamping member from rotating. In one embodiment, the means to contain movement of the floating/movable clamping member towards the mating locking surface on the second side of the frame increases tension along the length of the elongate member from about two to about five fold, preferably about two fold relative to the tension when the containing means is not present in the device.

The means to contain movement of the floating/moveable clamping member towards the mating locking surface on the second side of the frame may comprise temporarily retaining the floating/moveable clamping member for the purpose of first tensioning the elongate member using the second end.

The floating/movable clamping member may be temporarily retained with its rotation being prevented as well, by attachment to a notched member structured and adapted to hold the surface of the clamping member that is proximal to the second side of the frame away from the second side of the frame temporarily until the first tensioning is complete. When the tensioning is complete, the notched member is adapted to break away at the notches, and to allow for cinching the second end of the elongate member between the bar and the second side of the frame.

In another embodiment, the floating/moveable clamping member is temporarily retained by a pin that is structured and adapted to hold the surface of the clamping member that is proximal to the second side of the frame away from the second side of the frame temporarily until the first tensioning is complete and, to be removed to allow for cinching the second end of the elongate member between the clamping member and the second side of the frame.

In yet another embodiment, the floating/moveable clamping member is temporarily retained by a ball detent in the frame that is structured and adapted to hold the surface of the clamping member that is proximal to the second side of the frame away from the second side of the frame temporarily until the first tensioning is complete and, to undergo distortion in the frame when tension is increased in the elongate member to allow for cinching the second end of the elongate member between the bar and the second side of the frame.

In one embodiment, the floating/moveable clamping member is a locking bar or pin. As described elsewhere herein, the floating/moveable clamping member or locking bar can have any profile. In one embodiment, its profile is round, that is, it has a circular cross section. In the embodiment where the bar has a circular cross section, the bar attachment is adapted to prevent, in addition, rotational movement of the bar. Further, and independently, the surfaces of the floating/moveable clamping member or locking bar and the second side of the frame, that is the mating locking surface for the locking bar, may be textured or roughened to provide improved performance, that is, to secure the second end of the band better relative to when the surfaces are not textured, once the band is tensioned.

The floating/moveable clamping member or locking bar may be, in certain embodiments, attached outside of the frame at the second side of the frame via a locking bar attachment. In other embodiments, the floating/moveable clamping member or locking bar may be attached inside the frame at the second side of the frame via a locking bar attachment. In these latter embodiments, preferably, a support or buttress is provided inside the frame at the second frame side that includes an upper cam surface. In one embodiment, the locking bar attachment is a ribbon that has notches. The floating/moveable clamping member or locking bar is attached to the upper surface of the ribbon and the ribbon attaches the second frame side to the distal upper cam surface. Once first tensioning of the elongate member has been carried out, further increasing tension at the second end of the elongate member results in the notches breaking away and the second end of the elongate member is cinched between the surfaces of the second frame side and the locking bar. The clamping member can have any profile. In one embodiment, its profile is round, that is, it has a circular cross section. In the embodiment where the clamping member has a circular cross section, the ribbon is adapted to prevent, in addition, rotational movement of the bar. The cam surface allows for supplying more leverage to the hinging attachment mechanism such that the clamping member can be forced harder into and be better locked inside the upper cam surface of the support against the second frame side. In a further embodiment, the space between the locking bar and the inside of the first side of the frame and the space between the bar and the inside of the second side may be substantially similar and are sized to allow an elongate member or suture or band to pass through easily. Further and independently, the surfaces of the clamping member and the mating locking surface for the clamping member on the second side of the frame, may be textured or roughened to provide improved performance, that is, to secure the second end of the band better relative to then the surfaces are not textured, once the elongate member or band is tensioned. In the embodiment of the device where a needle is attached to the second end of the band, the locking bar is adapted to move away from the second frame side to a sufficient distance so as to allow the needle to pass around the locking bar.

As used herein, the tissue portions to be held in contact with one another in the present invention comprise biological tissue in the body, including, but not limited to, skin, tendon, bone, ligaments, blood vessels, and organs. In one embodiment, the tissue portions comprise sternal bone that has been cut for a procedure to access the thoracic cavity.

The dermal layer on top of the sternum is rather thin. Even when a surgeon employs only twisted wire to repair the sternum, some patients can feel that wire under their skin. Consequently, the profile of a closure device can have cosmetic as well as practical concerns. The dermal layer over the sternum on an average adult female is 5 to 10 mm thick. A device that is ~5 mm in height is sufficiently thick to be rather clearly seen in some adults. The profiles of the current inventive devices are spread out over a large surface area, resulting in a much more favorable aspect ratio, it will not be easily seen when viewing the patient from the outside.

A particularly advantageous feature of the invention is that the aspect ratio of the inventive device, defined as the height of the device above the tissue surface, divided by the length of the device, is less than or equal to approximately 0.50, and more preferably approximately 0.10. In addition, the maximum height or profile of the current inventive device at the frame preferably is about 4 mm to about 1 mm.

In certain preferred embodiments, the buckle or frame of the device is fabricated from either tempered stainless steel, spring tempered stainless steel or titanium.

In certain preferred embodiments of the present invention, the pins or bars or clamping members or ribbons of the device are fabricated from either tempered stainless steel, spring tempered stainless steel or titanium.

In certain preferred embodiments of the present invention, attachments or straps of the device are fabricated from either spring tempered stainless steel or titanium.

In one embodiment, the elongate member or band or suture of the present devices is sufficiently flexible to provide tension along its length. In yet another embodiment, the elongate member or band or suture is substantially flat. The elongate member or suture or band may be defined by that which is normally available. It may be woven fibers or a monofilament and can be any material. Accordingly, the band may comprise woven, braided, or knitted fibers or metals, or a monofilament, and can be made of any known suture material. The elongate member or band or suture may be of any shape, including, but not limited to, round, square, oval, flat (like a strap), or tubular. The shape of the elongate member, suture or band for particular embodiments will be discussed more fully herein below. In one embodiment of the inventive device, the elongate member preferably comprises flat or tape suture.

On one end of the elongate member or suture or band may be a needle or other receptacle to facilitate stitching or weaving in tissue or bone. Accordingly, in one embodiment, a needle may be secured to the second end of the band or suture of the device. Alternately, a needle may be secured to the first end or both ends of the suture.

As disclosed elsewhere herein, all of the embodiments illustrate buckles containing bands. There are many fasteners that rely on similar mechanisms for securing an elongated member around an object. This invention applies not only to buckles, but any mechanism that employs a floating/movable clamping element or member that is managed by the tension in the cinching tail. This invention would simply apply retaining concepts employed here on the floating/movable clamping element. Such a fastener may employ any number of different elongated members; bands, ropes, sutures, monofilaments, cables, braided structures, woven structures which could be made out of plastics, metals, re-absorbable plastics, ceramics, textiles, crystalline materials, and amorphous materials.

In one aspect of the invention, there is provided a tensioning device which comprises an elongate member, preferably a band, and a frame having first and second sides. The elongate member has a first end that is attachable to the first side of the frame and a second end that is releasably securable to the second side of the frame. The device further comprises a movable clamping member on the frame, which is adapted to secure the second end of the elongate member to the second side of the frame by cinching the second end of the elongate member between an engagement surface on the elongate member and a mating engagement surface on the second side of the frame. The mating engagement surface may be textured to further promoting clamping engagement. A restraining member is provided for restraining the clamping member to a first position spaced from the mating locking surface on the second side of the frame, when the restraining member is in a restraining orientation. The restraining member is movable out of the restraining orientation after the elongate member is tensioned to a predetermined level using the second end. The elongate member is tensioned to the aforementioned predetermined level and is secured to the second side of the frame, so that the elongate member establishes a path of tension along its length that extends linearly between the two ends of the elongate member. The tension along the path of tension is adapted to be greater when the restraining member is in the restraining orientation than when it has been moved out of the restraining orientation.

In one particular embodiment, the clamping member has a generally circular cross-section. In order to prevent the movable clamping member from rotating, a restraint is provided. In one embodiment, this restraint comprises a slot into which the end of the clamping member is inserted.

In one inventive approach, the restraining member comprises a ribbon having a point of weakness designed therein which is adapted to break at said predetermined tension level. This point of weakness preferably comprises a notch in the ribbon. In one embodiment adopting this inventive approach, the ribbon is attached between the frame and the movable clamping member, with the ribbon acting to prevent movement of the movable clamping member toward the mating engagement surface on the frame when intact. Its fracture at the point of weakness, when applied tension thereto reaches or exceeds the predetermined tension level, permits the movable clamping member to move from the first position toward the mating engagement surface to a second engaging position. In another embodiment adopting this inventive approach, the ribbon supports the movable clamping member in the first position when intact. Its fracture at the point of weakness when applied tension thereto reaches or exceeds the predetermined tension level, permits the movable clamping member to move along a cam surface to a second engaging position.

In another inventive approach, the restraining member comprises a removable pin.

In still another inventive approach, the frame further comprises a detent, and the moveable clamping member further comprises a ball engageable with the detent, wherein when the ball and the detent are engaged, they comprise the aforementioned restraining member. In this approach, the frame is adapted to distort sufficiently, upon application of tension thereto at the predetermined level, to dislodge the ball from the detent, so that the movable clamping member is unrestrained and free to move from the first position to a second engaging position.

The tensioning device described above is used, in certain preferred applications, in conjunction with a bone anchor, by attaching the frame to a proximal end of the bone anchor.

In another aspect of the invention, there is disclosed a method of repairing separated tissues using a tissue tensioning device, which comprises an elongate member having a first end and a second end, a frame having opposing first and second sides, a movable clamping member, and a restraining member, wherein the first end of the elongate member is attached to the first side of the frame. The inventive method comprises a step of applying tension to the second end of the elongate member so that the elongate member moves freely between spaced engaging surfaces on the movable clamping member and the second side of the frame, while the movable clamping member is restrained to a first non-engaging position by the restraining member. The method further comprises a step of moving the movable clamping member to a second position wherein the engaging surfaces on the movable clamping member and the second side of the frame are sufficiently engaged to clamp the elongate member in place. The moving step is performed by applying a predetermined tension level to the elongate member, so that the restraining member moves to a non-restraining orientation.

In one inventive approach, the moving step is performed by removing the restraining member from the device. In another approach, the moving step is performed by breaking the restraining member. In still another inventive approach, the moving step is performed by dislodging one portion of the restraining member from engagement with another portion of the restraining member.

The invention, together with additional features and advantages thereof, may best be understood by reference to the following description taken in conjunction with the accompanying illustrative drawings.

DETAILED DESCRIPTION OF THE INVENTION

Figure 1A:
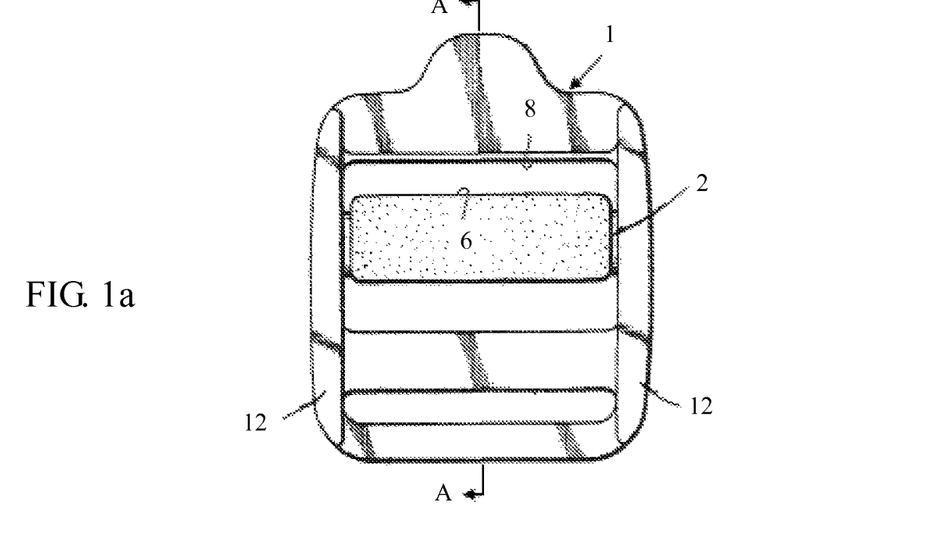
FIG. 1*a* is a top view of a common buckle.
Figure 1B:
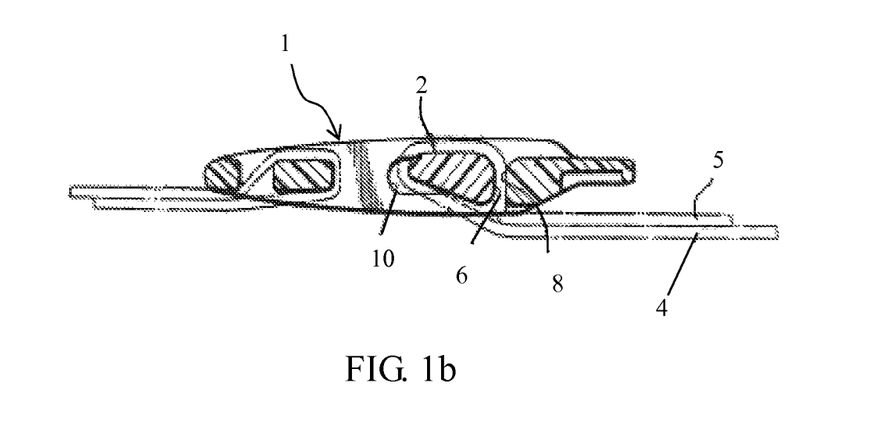
FIG. 1*b* is a cross sectional view of the buckle shown in FIG. 1*a*, fitted with a strap.

Referring now more particularly to the drawings, there is shown in FIGS. 1a and 1b a common buckle 1 and strap locking system. The common buckle 1, typically used in straps on bags, might be considered in this application for its variable tensioning abilities. A locking bar or clamping member 2 moves a surface 6 away from a surface 8 when a strap tail 5 is tensioned. As the strap tail 5 is tensioned, a strap tail 4 is pulled into the 6/8 surface interface. When strap tail 5 is released, strap tail 4 holds the dominate tension, which pulls the locking bar 2 so that the strap is pinched between the surfaces 6 and 8. This is the locked position of the buckle 1. Locking bar 2 is held in position by tabs on both of its ends that ride in a slot 10 which is cut out of a frame 12. The slot 10 is critical in the operation because it holds the face or surface 8 in engagement with the locking bar 2 so that it correctly pinches the strap up against surface 6. The variability of the tensions in strap tails 4 and 5 cause the locking bar to move in slot 10. The locking bar 2 naturally wants to even out these tensions by rotating in the slot 10. Flats are milled in the ends of the locking bar 2, in order to ride in slot 10 so that such rotation does not happen.

The reality of the movement of locking bar 2 in response to tension applied to tensioning strap tail 5 is minimal. It might be more accurate to say that the tensioning of strap tail 5 serves to relieve some pressure on the strap in the 6/8 surface interface such that strap movement is enabled. But strap movement is accomplished only when significant friction is overcome. If there were a way to further move locking bar 2 so that no pressure is put on the strap in the 6/8 surface interface, twice the tension would be realized in strap 4. A common buckle only transfers one-tenth of the tension placed on strap end 5 to strap end 4 due to the pressure put on the strap in the 6/8 surface interface. When the locking bar is held back such that there is no pressure in the 6/8 surface interface, approximately one-fifth of the tension placed on strap end 5 is realized in strap 4.

These mechanics define the objective of this invention, which comprises a mechanism that can hold the locking bar 2 such that the surface 6 is sufficiently spaced from the surface 8 so that no friction is imparted onto the strap by those respective surfaces. This mechanism exists as such while the buckle is being tensioned so that tensioning is easy. This same mechanism is able to be released so that, when desired, the surface 6 is allowed to float into the surface 8 as happens in a common buckle.

This inventive mechanism can operate in two ways. One is to place an object between surfaces 6 and 8 which would serve to hold them apart. This object is in place while tensioning and then is removed after the desired tension is achieved. For example, the mechanism may sense the tension in the strap and pull out the object when the desired tension is achieved. The other mode of operation is to pull on locking bar 2 with a restraining member so that the surface 6 is held away from the surface 8. This restraining member holds the surface 6 away from the surface 8 during tensioning of the strap and then is removed once the desired tension is achieved. The mechanism may sense tension in the strap and automatically release tension in the tension mechanism once the desired tension has been realized. Such a mechanism may be simply a ribbon with a notch in it. The notch is designed to fail at a specific tension that translates to the desired tension in the strap.

Figure 2:
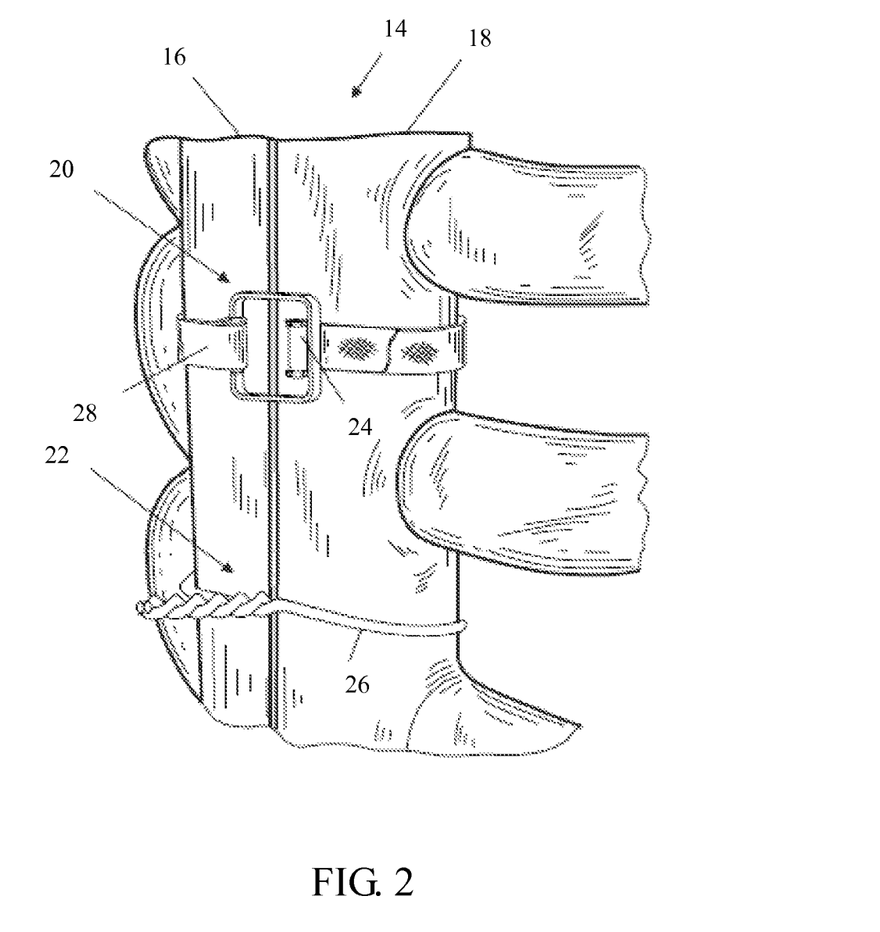
FIG. 2 is a top view showing how wires and bands might be used in binding sternal halves together for healing after open heart surgery

FIG. 2 shows a tensioning system application 14 for a single use buckle 24 employed after a sternal osteotomy procedure. Pictured is a sternum that has been cut down the middle (osteotomy) for surgical access to the chest cavity. This osteotomy is commonly performed in open heart procedures that require surgical access to heart valves and heart arteries. The sternum is cut into two halves 16 and 18 and the chest is separated to gain access to internal organs. After surgery, closure of the sternum must be performed to ensure proper healing. Wires 26 are commonly used to secure the sternal halves by wrapping them around the sternum and twisting them together at 22.

Wires have many complications when used in this capacity. Wires 26 are thin and cut into the bone. The forces realized by twisting the wires are highly variable. The twisted wires can untwist when the patient coughs. The wires can cyclically fail, fall off the sternum, and migrate to puncture arteries and organs. All of these failures are addressed by the use of a buckled band 20. The buckled band 20 comprises a band 28 wrapped around sternal halves 16 and 18 and terminating into buckle 24. The band 28 is tightened by cinching the band through the buckle 24. Buckled band 20 is ideal for the present invention as it is a single use buckle. Band 28 can be cinched through buckle 24 in a reduced friction environment, until a programmed force triggers a mechanism within the buckle and the buckle locks down onto the band.

Figure 3A:
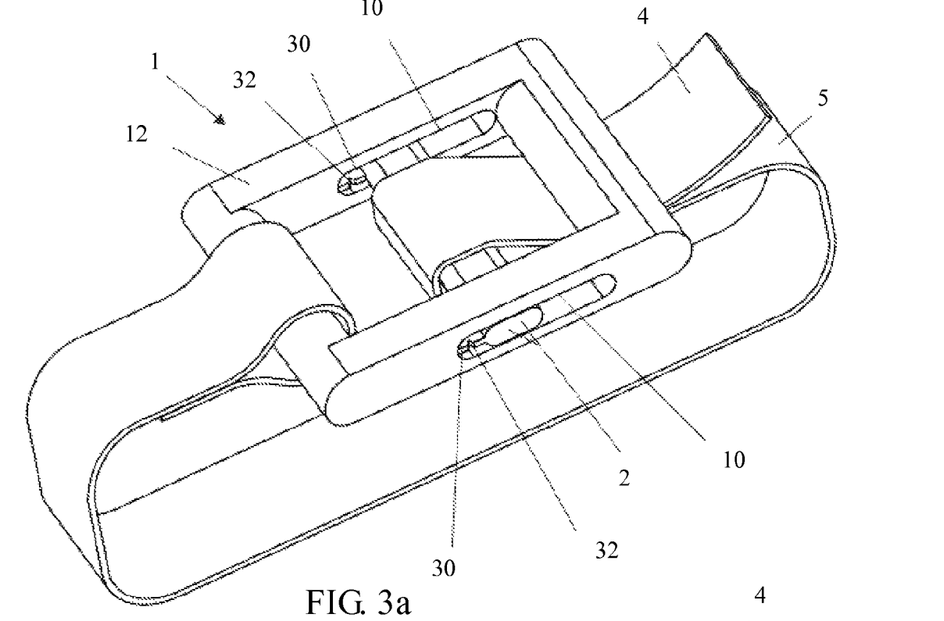
FIG. 3*a* is an isometric view of a low friction buckle tightening system in accordance with one embodiment of the invention, where notches are used to retain the clamping member.
Figure 3B:
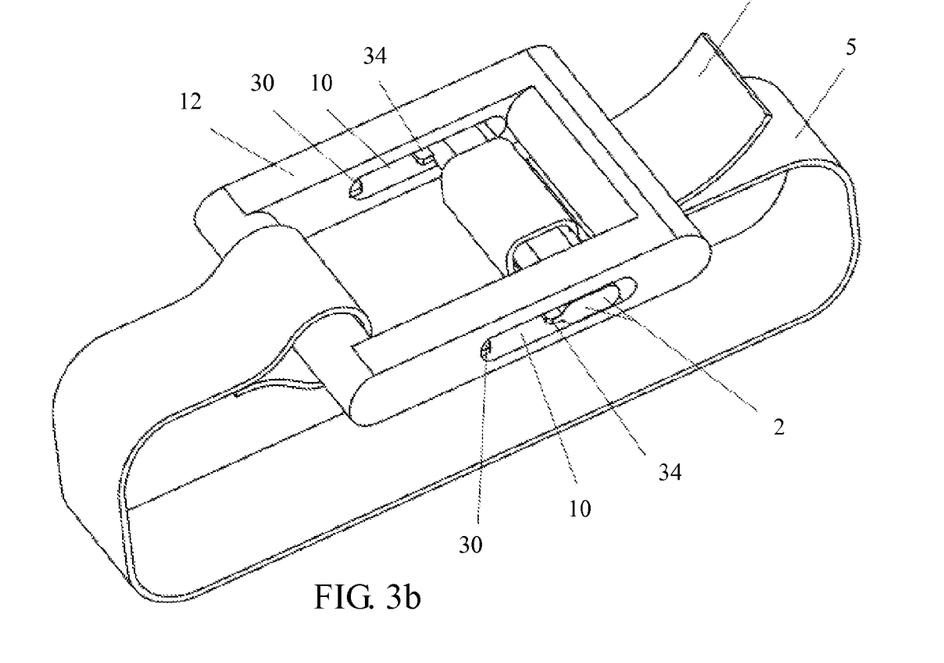
FIG. 3*b* is an isometric view of the embodiment in FIG. 3*a* where the notches are broken after first tensioning of the elongate member.

FIG. 3a shows an isometric view of a buckle 1 having a construction similar to that of the buckle shown in FIG. 1b. The buckle frame 12 is shown, as is a view of the clamping member or locking bar 2 with band tails 4 and 5 exiting buckle 1. A new element, a restraining member or ribbon 30, is shown to connect locking bar 2 to buckle frame 12. Ribbon 30 is placed on both ends of locking bar 2 such that it holds clamping surfaces 6 and 8 away from the band. This reduces the friction in the buckle, making the band much easier to cinch within the buckle. When enough cinching force is applied to the band, locking bar 2 will pull hard enough on ribbon 30 to break notch 32 contained within the ribbon as shown in FIG. 3b as ribbon pieces 30 and 34. After this time, locking bar 2 is free of ribbon 30 and can function as it would in a normal buckle. In one presently preferred embodiment, the ribbon 30 is fabricated of stainless steel, though other suitable biocompatible materials may be used as well.

Ribbon 30 restrains the clamping member 2 in a first non-engaging position, thereby allowing the clamping surfaces 6 and 8 to be sufficiently spaced so as not to impart friction onto the band. The tension realized in band tail 5 is equal to the tension in band tail 4 minus the friction internal to the buckle. Decreasing the friction internal to the buckle, as this invention does, increases the amount of tensioning force that can be translated from band tail 4 to band tail 5.

All of these embodiments illustrate buckles containing elongate members, or bands. There are many fasteners that rely on similar mechanisms for securing an elongated member around an object. This invention applies not only to buckles, but any mechanism that employs a floating/movable clamping element or member that is managed by the tension in the cinching tail. This invention simply applies retaining concepts employed here on the floating/movable clamping element. Such a fastener may employ any number of different elongated members; bands, ropes, sutures, monofilaments, cables, braided structures, woven structures which could be made out of plastics, metals, re-absorbable plastics, ceramics, textiles, crystalline materials, and amorphous materials.

Figure 4A:
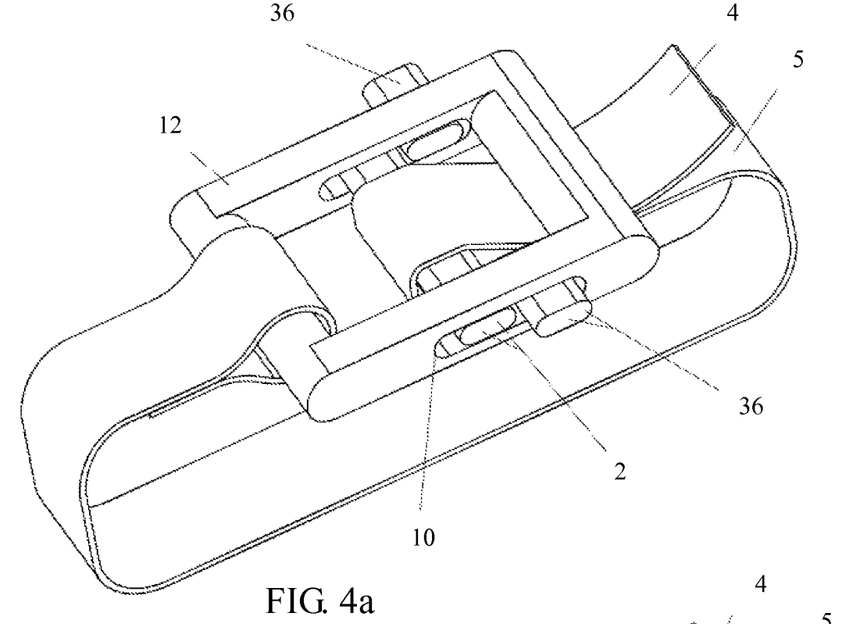
FIG. 4*a* is an isometric view of a low friction buckle tightening system in accordance with one embodiment of the invention where a pin is used to retain the clamping member.
Figure 4B:
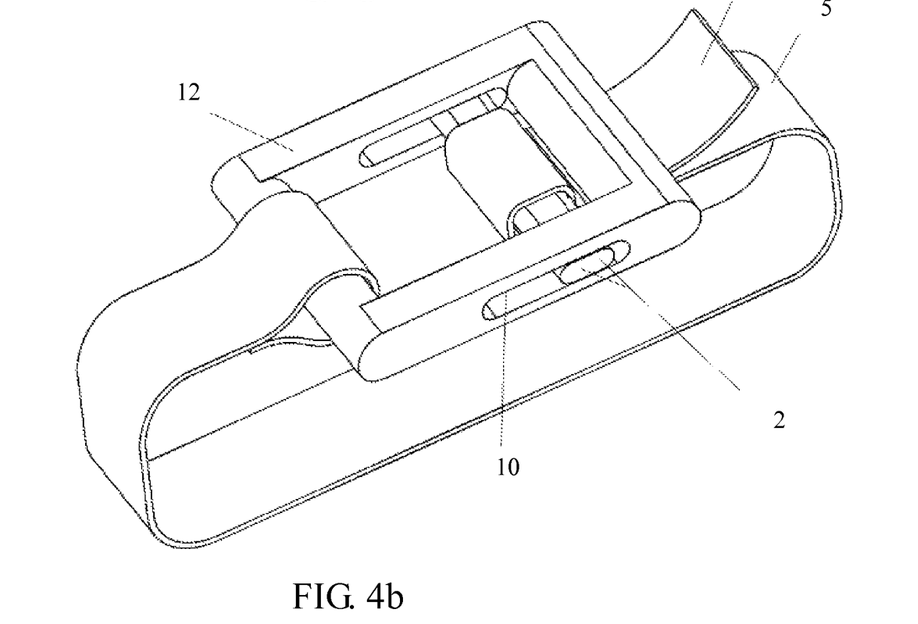
FIG. 4*b* is an isometric view of the embodiment in FIG. 4*a* where the pin is removed after first tensioning of the elongate member.

FIG. 4a shows another embodiment of the invention which utilizes a pin 36 instead of the ribbon 30 as the retaining member for retaining locking bar 2 in its first non-engaging position. The pin 36 is placed on both ends of the locking bar 2 such that it holds clamping surfaces 6 and 8 away from the band. This reduces the friction in the buckle making the band much easier to cinch within the buckle. When the desired tension is realized in the band tail 5 by pulling on band tail 4, pins 36 are removed to allow locking bar 2 to function in slot 10 as it would in a normal buckle (see FIG. 4b).

Figure 5A:
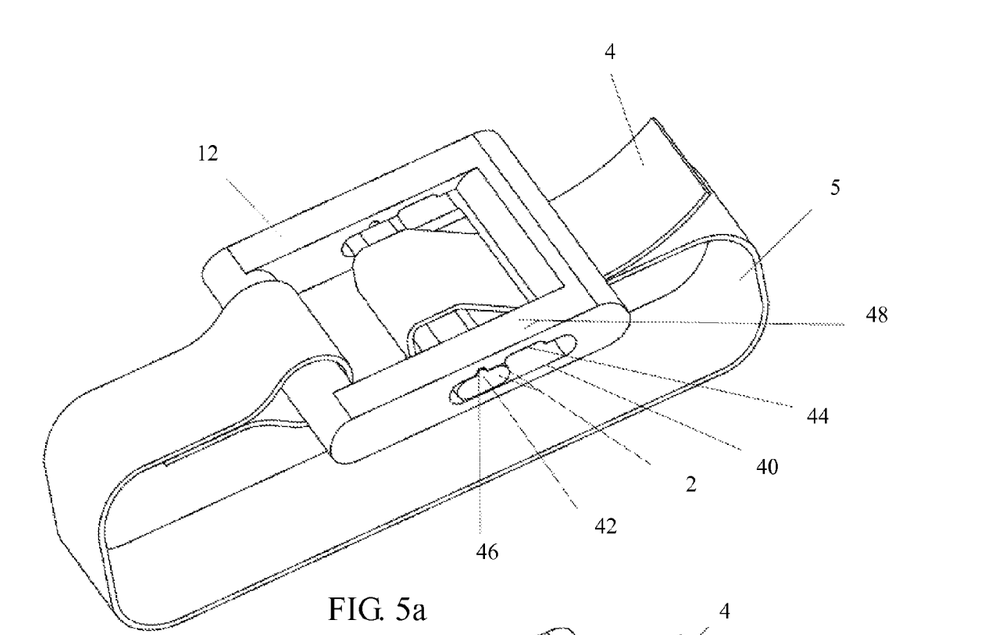
FIG. 5*a* is an isometric view of a low friction buckle tightening system in accordance with one embodiment of the invention where a ball detent is used to retain the clamping member.
Figure 5B:
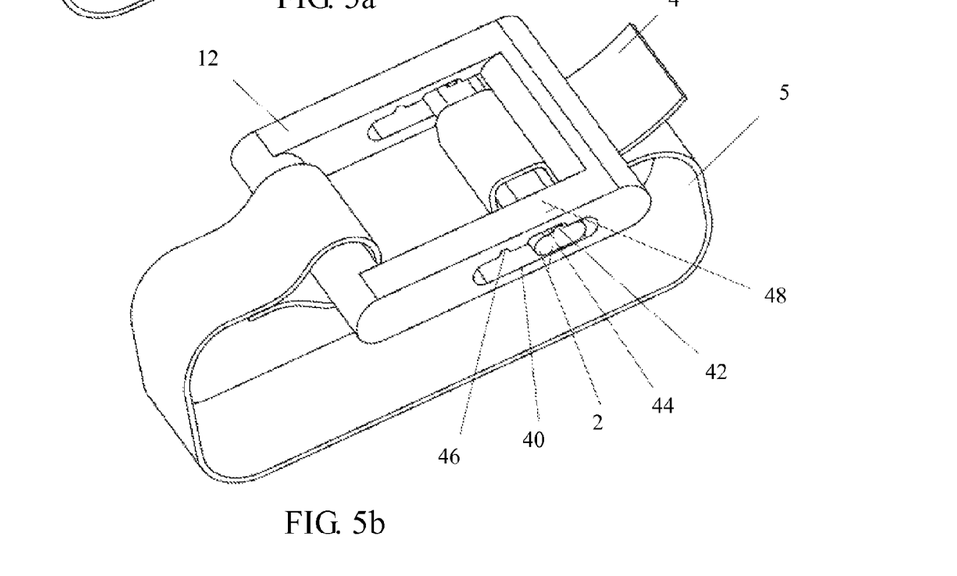
FIG. 5*b* is an isometric view of the embodiment in FIG. 5*a* where the detent is deformed after first tensioning of the elongate member.

FIG. 5a shows another embodiment of the invention, which utilizes a concept similar to a ball detent to retain the locking bar 2 while tensioning the band tail 4. Only one side of the buckle is shown, however the other side of the buckle is the mirror image of that shown. Ball 42 is attached to the locking bar 2 for the purposes of residing in detent 46. These two elements 42 and 46 together comprise the aforementioned retaining member. Locking bar 2 slides in a slot 40, which has a detent 46 and a detent 44. The top of the slot 40 has a member 48 which is able to flex. When tensioning the buckle, increased tension loads locking bar 2 so that it distorts member 48. At the desired tension, member 48 is designed to flex so that ball 42 is able to slide out of detent 46 and into detent 44 as is shown in FIG. 5b. Detent 44 is long, thereby allowing the locking bar 2 to slide as it would in a normal buckle. This allows the buckle to operate normally from this time forward.

Figure 6A:
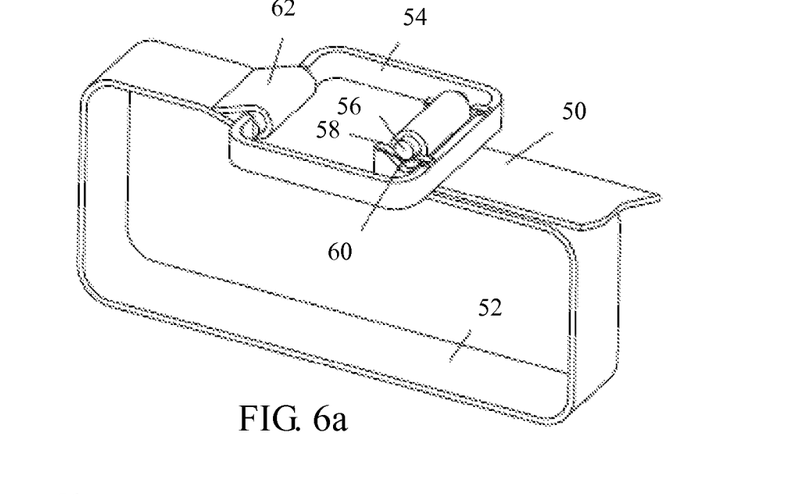
FIG. 6*a* is an isometric view of a low friction buckle tightening system in accordance with an embodiment of the present invention, wherein the first end of the elongate member is attached to a buckle and the second end is ready to be secured after first tensioning.
Figure 6B:
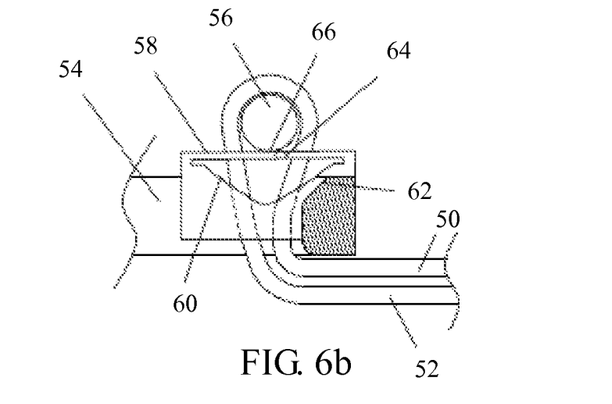
FIG. 6*b* is a cross sectional view of the buckle system shown in FIG. 6*a*, with the notched means for separating the clamping member from the second side of the frame.
Figure 6C:
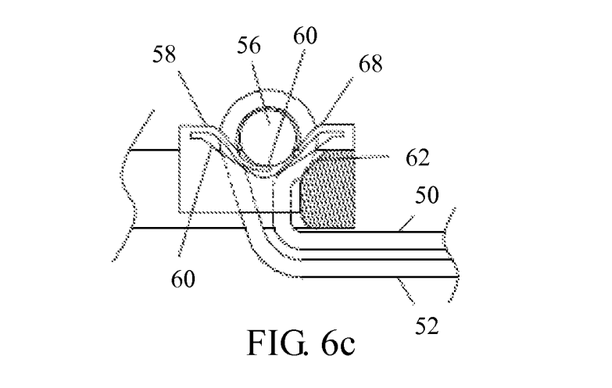
FIG. 6*c* is a cross sectional view of the buckle system shown in FIG. 6*a* after first tensioning, with the notches broken and where the clamping member has cinched the elongate member between itself and the second side of the frame.

FIGS. 6a-6c shows yet another embodiment of the invention. This embodiment shows how the principle of temporarily retaining the locking bar for the purpose of tensioning can be achieved with the disclosed mechanisms outside of the typical slot/locking bar buckle design. The basic tenets of a buckle require there to be a floating/moveable clamping or locking member, a mating locking surface attached to a structure, a means within this structure to contain movement of the floating/moveable clamping or locking member so that it only moves into and away from the mating locking surface, and a means for keeping the floating/moveable clamping or locking member from rotating. As stated in these terms this invention temporarily retains the floating/moveable clamping or locking member away from its mating surface. FIG. 6a shows a buckle that has a pin 56 for its floating/moveable clamping or locking member, surface 62 for its mating locking surface on structure 54, a cam surface 60 for containing movement of pin 56, and a ribbon 58 (the retaining member) to keep pin 56 from rotating. (See FIG. 6b for pin 56 weld location 66 to ribbon 58.) Pulling on the band end 50 causes the pin 56 to ride up on the cam surface 60, thereby temporarily releasing its hold on the band and allowing cinching of the band.

FIG. 6b shows pin 56 being held away from the mating locking surface 62 by means of ribbon 58, which contains an engineered weak point such as a notch 64. It is clear that the pin 56 is being held sufficiently away from the mating locking surface 62 so as to not have any associated engagement friction. In being structured thus, the band tail 50 can easily tension band 52. When a desired tension has been realized, sufficient forces are imposed on the ribbon 58 so that the notch 64 fails.

FIG. 6c shows what happens after the notch 64 fails. Ribbon 58 breaks into two pieces leaving a ribbon remnant 68. The pin 56 rides down the cam surface 60 to settle against mating locking surface 62 through the band. Now the buckle operates as it would without the invention; pulling on band tail 50 pushes the pin up the cam surface to allow pin 56 to move away from mating locking surface 62, thereby allowing band 52 to move through the buckle.

Structured as described in the foregoing, this invention provides a means to allow a buckle to significantly increase its tensioning performance. Breakaway mechanisms allow this increase in performance to exist only for the first tensioning. Pin type mechanisms may be reused, thus allowing the repeated advantage of tensioning without the binding friction found in normal buckles. There are also ways that the ball-detent mechanism may be reset as well.

The tissue portions to be held in contact with one another in the present invention comprise biological tissue in the body, including, but not limited to, skin, tendon, bone, ligaments, blood vessels, and organs. In one embodiment, the tissue portions comprise sternal bone that has been cut for a procedure to access the thoracic cavity. The suture may comprise woven, braided, or knitted fibers or metals, or a monofilament, and can be made of any known suture material. The suture may be of any shape, including, but not limited to, round, square, oval, flat (like a strap), or tubular. The shape of the suture for particular embodiments will be discussed more fully herein below. In one embodiment of the inventive device, the suture preferably comprises flat or tape suture.

In certain preferred embodiments, the buckle or frame of the device, as well as the pins or bars of the device, are fabricated from either tempered stainless steel, spring tempered stainless steel or titanium.

Although round bars or pins are shown up against flat surfaces in certain embodiment, contoured pins with contoured mating surfaces on the pin and frame respectively, may be used to increase the buckle's holding performance. The mating surfaces, contoured or otherwise, may be further roughened or textured if more performance or better grip or holding is required.

In certain preferred embodiments of the present invention, attachments or straps of the device are fabricated from either spring tempered stainless steel or titanium.

Although round bars or pins are shown in this embodiment, contoured pins with contoured mating surfaces on the pin and frame respectively, may be used to increase the buckle's holding performance. The mating surfaces, contoured or otherwise, may be further roughened or textured if more performance or better grip or holding is required.

Figure 7A:
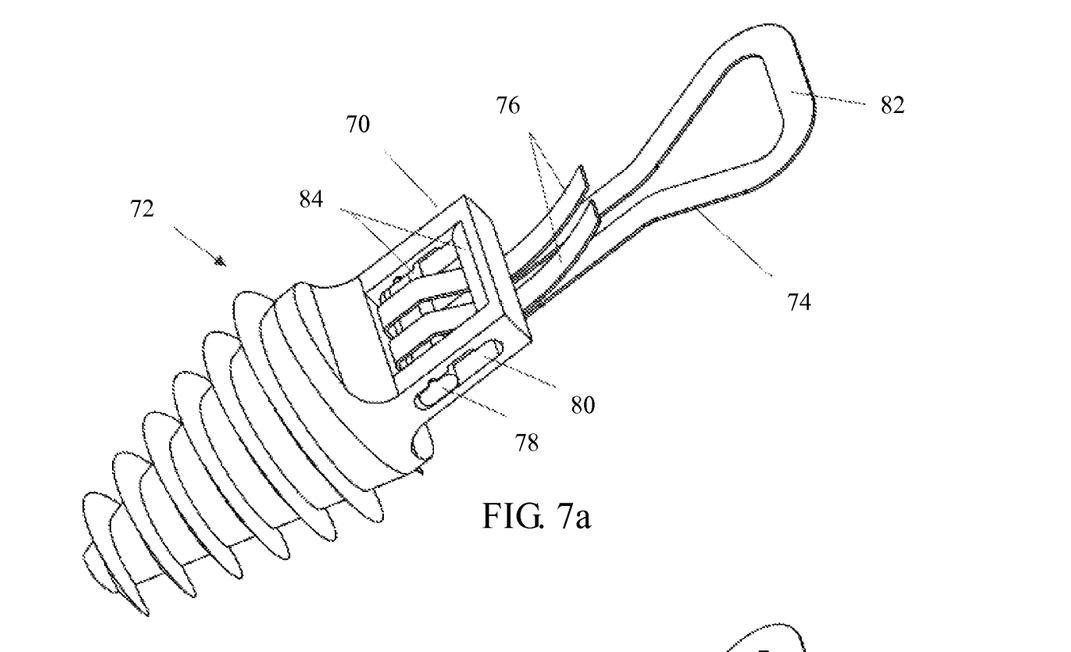
FIG. 7*a* is an isometric view of an embodiment of the invention that is incorporated into a bone anchor, wherein a lockbar is in its distal position so that sutures may pass freely through the clamping member.
Figure 7B:
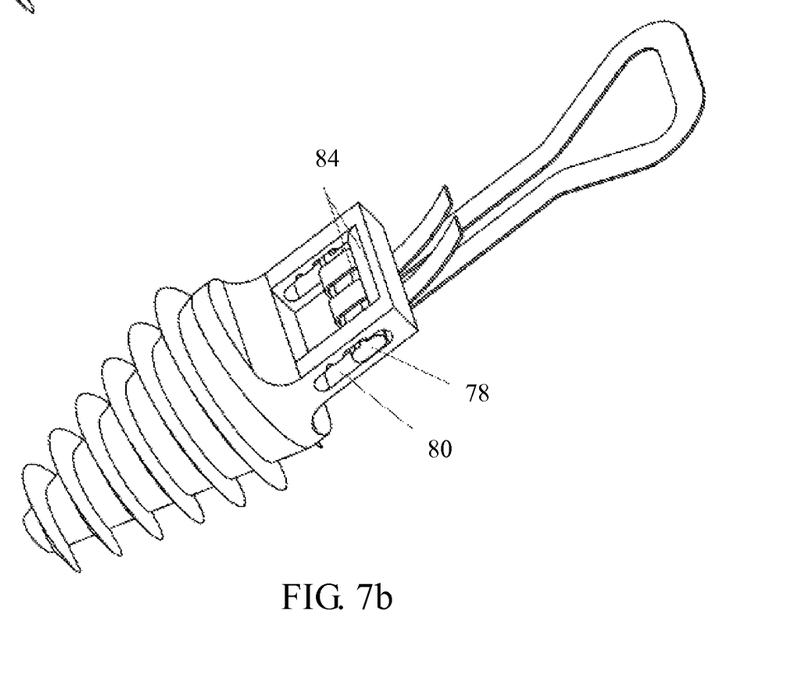
FIG. 7b is a view similar to FIG. 7a, wherein the lockbar is in its proximal position so that the clamping surfaces fully engage suture within their interface.

Still another alternative embodiment of the invention is illustrated in FIGS. 7a and 7b. In this embodiment, a buckle 70 is attached to a proximal end of a threaded bone anchor 72. Suture 74 is tensioned by suture tails 76. A lockbar 78 slides in a slot 80. Suture is looped or tied into tissue at 82.

FIG. 7a illustrates the buckle 70, wherein the lockbar 78 is in its distal position, held there by a ball on the lockbar and a detent in slot 80. This embodiment function in a manner very similar to the embodiment shown in FIGS. 5a and 5b. This position of the lockbar 78 enables sutures to pass freely between clamping surfaces 84. FIG. 7b illustrates the buckle 70, wherein the lockbar 78 is in its proximal position, free to slide in the slot 80 so that the clamping surfaces fully engage suture within their interface.

While the bone anchor embodiment illustrated in FIGS. 7a and 7b is shown in connection with a threaded bone anchor, and further in connection with an inventive mechanism as shown in the embodiment of FIGS. 5a and 5b, the inventive concept is suitable for use with any known bone anchor type, as well as with any of the inventive embodiments disclosed in FIGS. 2-6c herein.

While the inventive concept is disclosed as being particularly adapted for use in repairing the sternum after a thoracic cavity procedure, it is, of course, applicable to a great many other procedures requiring repair of bodily tissue, particularly bone.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention, which is to be limited only in accordance with the following claims.

What is claimed is:

1. A tensioning device comprising:
   an elongate member;
   a frame having first and second sides, said elongate member having a first end that is attachable to the first side of said frame and a second end that is releasably securable to the second side of said frame;
   a movable clamping member on said frame which is adapted to secure the second end of said elongate member to the second side of said frame by cinching the second end of said elongate member between an engagement surface on the elongate member and a mating engagement surface on said second side of the frame; and
   a restraining member for restraining said clamping member to a first position spaced from said mating locking surface on said second side of the frame, when the restraining member is in a restraining orientation, said restraining member being movable out of said restraining orientation after said elongate member is tensioned to a predetermined level using said second end, the restraining member comprising a ribbon having a point of weakness designed therein which is adapted to break at said predetermined tension level;
   wherein when said elongate member is tensioned to said predetermined level and is secured to the second side of said frame, said elongate member establishes a path of tension along its length that extends linearly between the two ends of the elongate member.

2. The device of claim 1, wherein the tension along said path of tension is greater when said restraining member is in said restraining orientation than when it has been moved out of said restraining orientation.

3. The device of claim 1, wherein said clamping member has a generally circular cross-section.

4. The device of claim 3, and further comprising a restraint for preventing said movable clamping member from rotating.

5. The device of claim 1, wherein said elongate member is a band.

6. The device of claim 1, wherein the point of weakness comprises a notch in said ribbon.

7. The device as recited in claim 1, wherein said ribbon is attached between said frame and said movable clamping member, said ribbon acting to prevent movement of the movable clamping member toward the mating engagement surface on the frame when intact, and further wherein its fracture at the point of weakness when applied tension thereto reaches or exceeds said predetermined tension level permits the movable clamping member to move from said first position toward the mating engagement surface to a second engaging position.

8. The device as recited in claim 1, wherein said ribbon supports said movable clamping member in said first position when intact, and further wherein its fracture at the point of weakness when applied tension thereto reaches or exceeds said predetermined tension level permits the movable clamping member to move along a cam surface to a second engaging position.

9. The device as recited in claim 1 wherein the mating locking surface on said second side of the frame is textured.

10. The device as recited in claim 1, wherein said frame is attached to a proximal end of a bone anchor.

11. A method of repairing separated tissues using a tissue tensioning device comprising an elongate member having a first end and a second end, a frame having opposing first and second sides, a movable clamping member, and a restraining member, wherein the first end of the elongate member is attached to the first side of the frame, said method comprising:
   applying tension to the second end of the elongate member so that the elongate member moves freely between spaced engaging surfaces on the movable clamping member and the second side of the frame, while the movable clamping member is restrained to a first non-engaging position by the restraining member; and
   moving the movable clamping member to a second position wherein the engaging surfaces on the movable clamping member and the second side of the frame are sufficiently engaged to clamp the elongate member in place, said moving step being performed by applying predetermined tension level on the elongate member, so that the restraining member breaks and is thereby moved to a non-restraining orientation.

12. The method as recited in claim 11, wherein said moving step is performed by dislodging one portion of the restraining member from engagement with another portion of the restraining member.

* * * * *